(12) United States Patent
Smith (10) Patent No.: US 11,707,633 B2
(45) Date of Patent: Jul. 25, 2023

(54) VARIABLE SOUND SYSTEM FOR AUDIO DEVICES

(71) Applicant: Physio-Control, Inc., Redmond, WA (US)

(72) Inventor: Robert Eugene Smith, Lynnwood, WA (US)

(73) Assignee: Physio-Control, Inc., Redmond, WA (US)

(*) Notice: Subject to any disclaimer, the term of this patent is extended or adjusted under 35 U.S.C. 154(b) by 38 days.

(21) Appl. No.: 17/669,738

(22) Filed: Feb. 11, 2022

(65) Prior Publication Data

US 2022/0212020 A1     Jul. 7, 2022

Related U.S. Application Data

(63) Continuation of application No. 17/061,556, filed on Oct. 1, 2020, now Pat. No. 11,247,062, which is a continuation of application No. 16/576,246, filed on Sep. 19, 2019, now Pat. No. 10,792,507, which is a continuation of application No. 16/267,182, filed on
(Continued)

(51) Int. Cl.
| | |
|---|---|
| *H03G 9/00* | (2006.01) |
| *H03G 9/02* | (2006.01) |
| *G10L 19/02* | (2013.01) |
| *H03G 3/32* | (2006.01) |
| *H03G 3/24* | (2006.01) |
| *A61N 1/39* | (2006.01) |

(Continued)

(52) U.S. Cl.
CPC .............. *A61N 1/3993* (2013.01); *A61N 1/39* (2013.01); *A61N 1/3904* (2017.08); *H03G 9/005* (2013.01); *H03G 9/02* (2013.01); *G10L 19/02* (2013.01); *G10L 21/02* (2013.01); *G10L 21/0332* (2013.01); *H03G 3/24* (2013.01); *H03G 3/32* (2013.01); *H03G 9/025* (2013.01); *H04R 2430/01* (2013.01)

(58) Field of Classification Search
CPC .......... H03G 3/32; H03G 9/005; H03G 9/025; H03G 3/24; H03G 9/02; H04R 2430/01; G10L 21/02; G10L 19/02; G10L 21/0332; A61N 1/39; A61N 1/3904; A61N 1/3993
USPC ........................................................ 381/107
See application file for complete search history.

(56) References Cited

U.S. PATENT DOCUMENTS

| | | |
|---|---|---|
| 4,454,609 A | 6/1984 | Kates |
| 5,790,671 A | 3/1998 | Cooper |

(Continued)

FOREIGN PATENT DOCUMENTS

| | | |
|---|---|---|
| WO | WO2006020427 A2 | 2/2006 |

OTHER PUBLICATIONS

Office Action for U.S. Appl. No. 14/526,108, dated May 3, 2016, Smith, "Variable Sound System for Medical Devices," 34 pages.
(Continued)

*Primary Examiner* — Paul Kim
(74) *Attorney, Agent, or Firm* — Lee & Hayes, P.C.

(57) ABSTRACT

A system capable of self-adjusting both sound level and spectral content to improve audibility and intelligibility of electronic device audible cues. Audible cues are stored as sound files. Ambient noise is detected, and the output of the audible cues is altered based on the ambient noise. Various embodiments include processed sound files that are more robust in noisy environments.

20 Claims, 8 Drawing Sheets

Related U.S. Application Data

Feb. 4, 2019, now Pat. No. 10,441,806, which is a continuation of application No. 15/617,862, filed on Jun. 8, 2017, now Pat. No. 10,195,452, which is a continuation of application No. 14/526,108, filed on Oct. 28, 2014, now Pat. No. 9,713,728.

(60) Provisional application No. 61/897,136, filed on Oct. 29, 2013.

(51) Int. Cl.
*G10L 21/02* (2013.01)
*G10L 21/0332* (2013.01)

(56) References Cited

U.S. PATENT DOCUMENTS

| | | | |
|---|---|---|---|
| 5,792,190 | A | 8/1998 | Olson et al. |
| 6,301,502 | B1 | 10/2001 | Owen et al. |
| 7,548,781 | B2 | 6/2009 | Vaisnys et al. |
| 8,165,314 | B2 | 4/2012 | Sawashi |
| 8,280,730 | B2 | 10/2012 | Song et al. |
| 8,331,574 | B2 | 12/2012 | Powers |
| 8,964,998 | B1 | 2/2015 | McClain |
| 9,225,310 | B1 | 12/2015 | Lukin |
| 9,713,728 | B2 | 7/2017 | Smith |
| 2008/0091416 | A1 | 4/2008 | Kim et al. |
| 2009/0092260 | A1 | 4/2009 | Powers |
| 2010/0202622 | A1 | 3/2010 | Hardee et al. |
| 2010/0166225 | A1* | 7/2010 | Watanabe ............ H03G 3/32 381/107 |
| 2011/0125494 | A1 | 5/2011 | Alves et al. |
| 2011/0267180 | A1 | 11/2011 | Ferringo et al. |
| 2012/0101819 | A1 | 1/2012 | Heiman et al. |
| 2013/0343585 | A1 | 12/2013 | Bennett et al. |
| 2014/0219478 | A1 | 3/2014 | Takahashi et al. |
| 2021/0085991 | A1 | 3/2021 | Smith |

OTHER PUBLICATIONS

Office Action for U.S. Appl. No. 15/617,862, dated May 17, 2018, Smith, "Variable Sound System for Medical Devices," 21 pages.
Office Action for U.S. Appl. No. 15/617,862, dated Aug. 25, 2017, Smith, "Variable Sound System for Medical Devices," 21 pages.
Office Action for U.S. Appl. No. 16/576,246, dated Oct. 22, 2019, Smith, "Variable Sound System for Audio Devices," 32 pages.
Office Action for U.S. Appl. No. 14/526,108, dated Nov. 23, 2016, Smith, "Variable Sound System for Medical Devices," 43 pages.
Office action for U.S. Appl. No. 16/576,246, dated Mar. 2, 2020, Smith, "Variable Sound System for Audio Devices ", 24 pages.
Unknown, The Art and Science of the Sound Lab, Blog, post, dated Aug. 5, 2013, 3 pgs.

\* cited by examiner

FIG. 1   *DEFIBRILLATION SCENE*

Fig. 6                                                                Audible Cue Fig. 7                                                                Masking Signal

Fig. 8

Audible Cue inaudible over masking signal

Fig. 9

Alert Cue with harmonics

Fig. 10

Alert Cute still audible despite Masking Signal

Fig. 11

Alert Cue with harmonics and Masking Signal with harmonics

Fig. 12

Alert Cue with altered in accordance with Critical Band (CB) teachings

Fig. 13

CB Altered Alert Cue with Masking Signal

Fig. 14

CB Altered Alert Cue
with Masking Signal
Having Harmonics

VARIABLE SOUND SYSTEM FOR AUDIO DEVICES

CROSS REFERENCE TO RELATED APPLICATIONS

This application is a continuation of U.S. patent application Ser. No. 17/061,556, filed Oct. 1, 2020, which is a continuation of U.S. patent application Ser. No. 16/576,246, filed Sep. 19, 2019, now U.S. Pat. No. 10,792,507 issued Oct. 6, 2020, which is a continuation of U.S. patent application Ser. No. 16/267,182, filed Feb. 4, 2019, now U.S. Pat. No. 10,441,806 issued Oct. 15, 2019, which is a continuation of U.S. patent application Ser. No. 15/617,862, filed Jun. 8, 2017, now U.S. Pat. No. 10,195,452, issued on Feb. 5, 2019, which is a continuation of U.S. patent application Ser. No. 14/526,108, filed Oct. 28, 2014, now U.S. Pat. No. 9,713,728 issued Jul. 25, 2017, which claims the benefit of and priority to U.S. Provisional Patent Application No. 61/897,136, filed Oct. 29, 2013, and titled "Variable Sound System for Medical Devices," each of which is incorporated herein by reference in their entirety.

TECHNICAL FIELD

The disclosed subject matter pertains to the area of electronic devices.

BACKGROUND INFORMATION

The use of field-deployed medical devices, such as portable defibrillators, is achieving widespread acceptance. Such devices are designed to be used in high-stress environments by people who may not be well trained. Thus, the medical devices commonly provide audible cues to the user to guide the use of the medical device. However, such medical devices may be deployed in greatly disparate noise environments ranging from very quiet, such as an office setting, to very loud, such as a railroad station. Thus, the audible cues must compete with drastically different ambient sounds that interfere with the intelligibility of the audible cues.

Portable devices are also constrained by size, weight, and power limitations.

SUMMARY OF EMBODIMENTS

Disclosed is a system capable of self-adjusting both sound level and spectral content to improve audibility and intelligibility of medical device audible cues. Audible cues are stored as sound files. Ambient noise is detected, and the output of the audible cues is altered based on the ambient noise. Various embodiments include processed sound files that are more robust in noisy environments.

DETAILED DESCRIPTION OF EMBODIMENTS

Generally described, embodiments are directed at discovering information about an ambient sound environment, such as sound level, or spectral content or both, and exploiting psycho-acoustic principles of the human auditory system to enhance the ability to distinguish intended audible cues from ambient noise. Specific embodiments exploit masking and critical bands in the basilar membrane. Combining a measurement of the ambient sound environment and a psycho-acoustically driven knowledge base of the spectrum, a sound source is chosen or modified as necessary to improve resistance to auditory masking, thereby improving the audibility of alerts and alarms, and intelligibility of voice prompts. Although particularly applicable to the area of portable medical devices, the disclosed subject matter has applicability to many other areas, such as the automotive industry, or the like.

Figure 1:
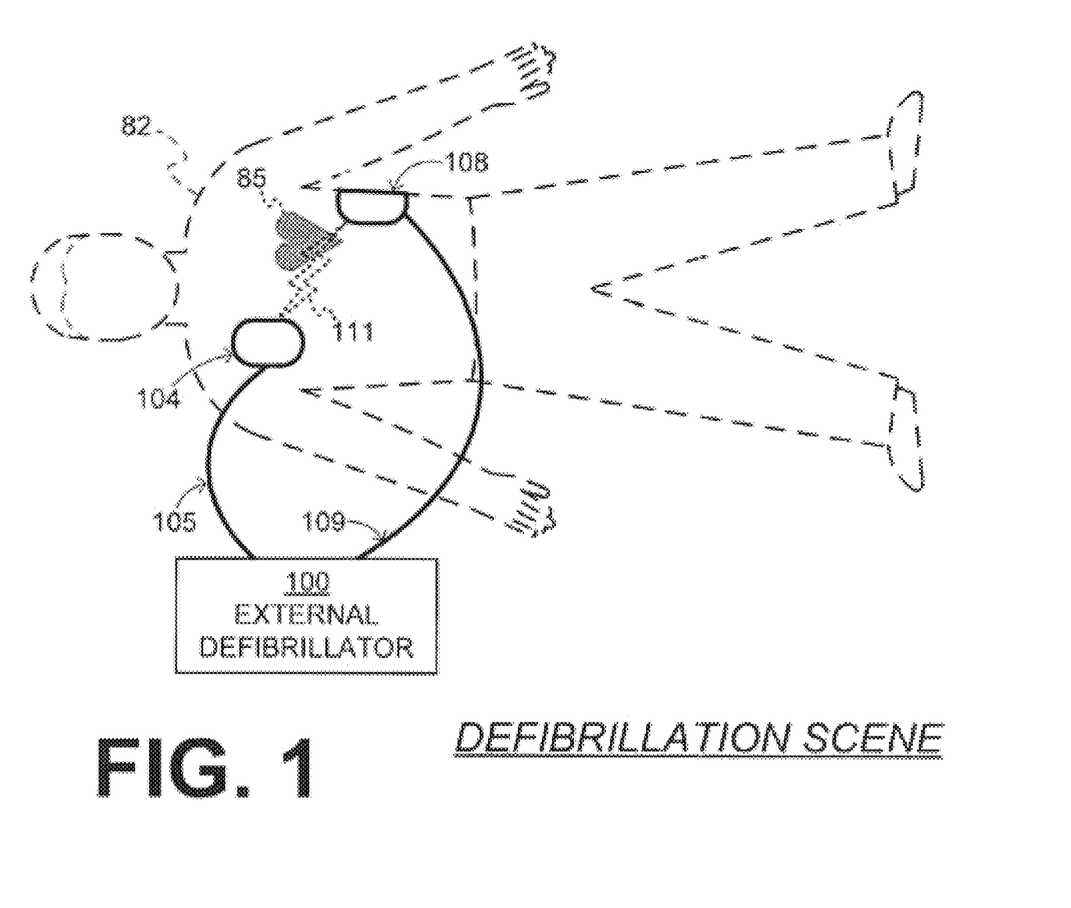
FIG. 1 is a diagram of a scene where an external defibrillator is used to save the life of a person.

FIG. 1 is a diagram of a defibrillation scene. A person 82 is lying supine. Person 82 could be a patient in a hospital, or someone found unconscious and turned on his or her back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82. Defibrillator 100 can be one of different types, each with different sets of features and capabilities. The set of capabilities of defibrillator 100 is determined by planning who would use it, and what training they would be likely to have.

In use, defibrillator 100 provides audible cues to inform the rescuer of the steps to properly operate defibrillator 100. However, the defibrillation scene may occur in any one of many different environments having greatly divergent audible characteristics. In other words, the defibrillation scene may occur in a relatively quiet indoor environment, or it may occur in a relatively loud outdoor environment, or anything in between. Operating in various noise environments poses problems for selecting the appropriate format to output the audible cues. In loud environment the audible cues can be difficult to hear if too quiet. In quiet environments, the audible cues can be harsh on the ear and even quasi painful if too loud. Either case (quiet or loud environments) both result in degradation in speech intelligibility under the foregoing conditions. Disclosed are embodiments that enable the defibrillator 100 to automatically adjust the sound output of the audible cues based on the ambient noise environment.

Generally stated, when two sounds are closely related in time and frequency such that they are within a critical band of each other, the sound with the lower sound level will be masked by the one with the higher sound level. This phenomenon is illustrated with reference to the sample spectrograms of FIGS. 6-8. In the spectrograms, the "X" axis denotes time; 0 to 10 seconds. The "Y" axis represents frequency; 0 to 4000 Hz. Sound levels are represented by brightness on the spectrogram; brighter is higher sound level, darker is lower sound level. For simplicity of discussion, simple sounds will be presented. However, the concepts extend equally to complex sounds including music and speech.

Figure 5:
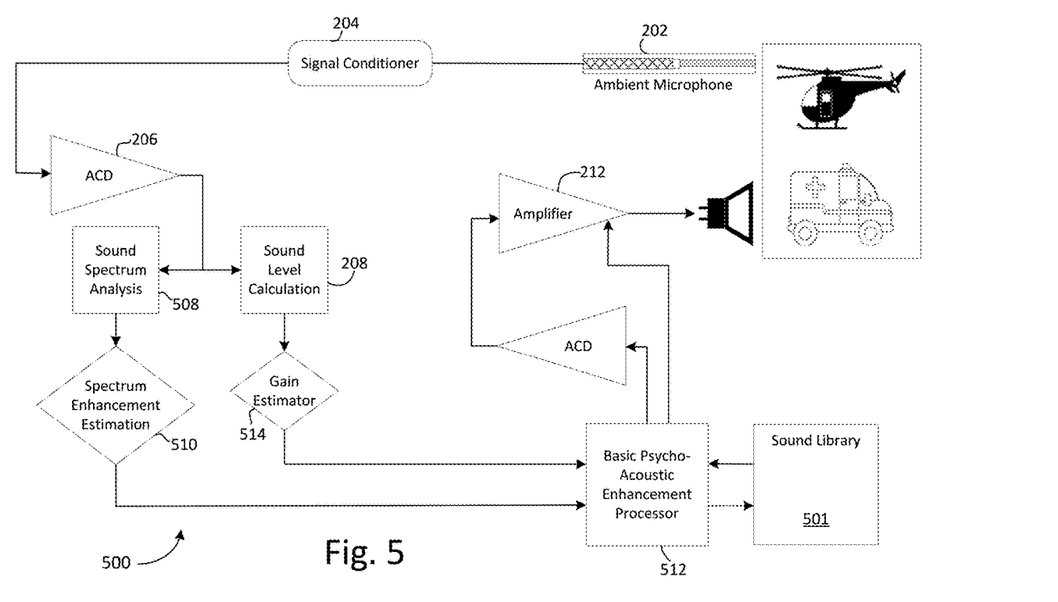
FIG. 5 a functional block diagram illustrating components of a third alternative embodiment that improves on the first and second alternative embodiments of FIGS. 3 and 4.
Figure 6:
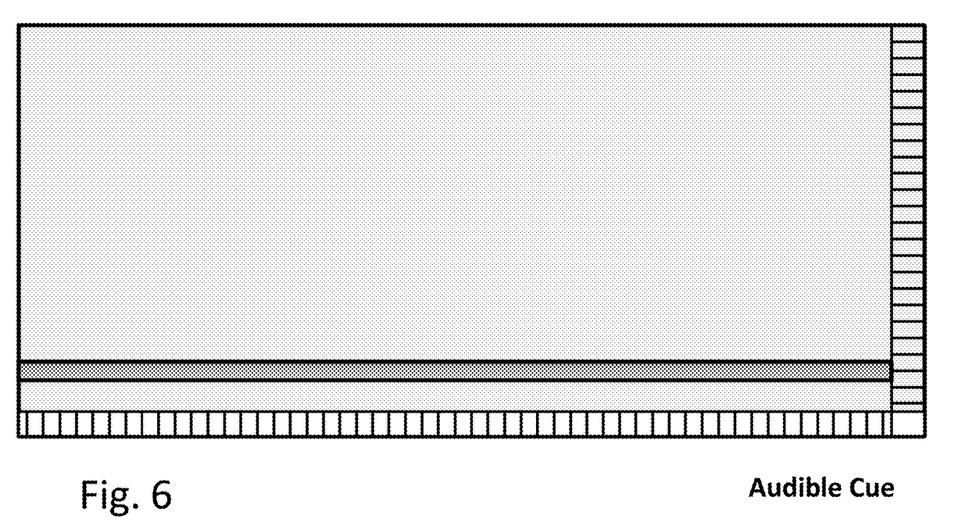
FIG. 6 is a sample spectrogram illustrating a 440 Hz pure sine tone, representing an audible cue.
Figure 7:
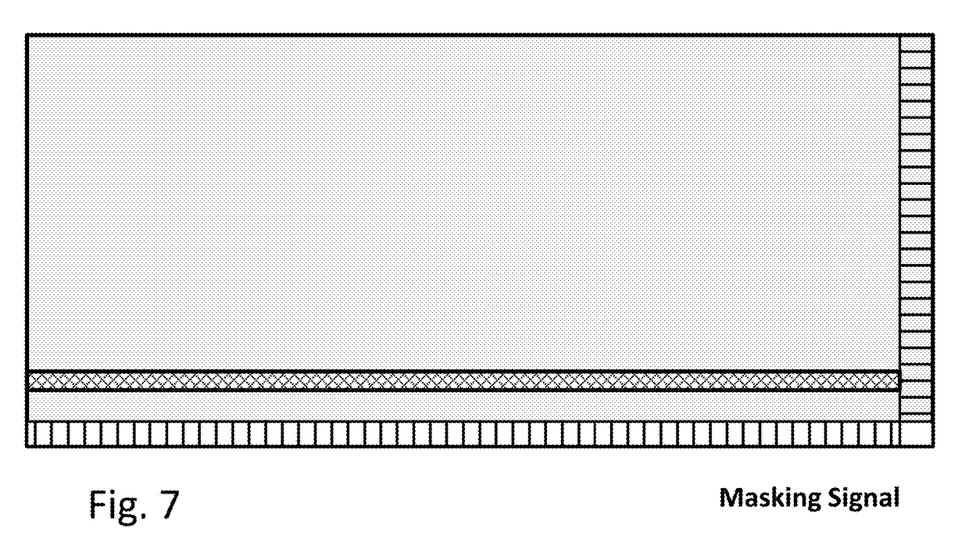
FIG. 7 is a spectrogram illustrating a 400 Hz masker signal.
Figure 8:
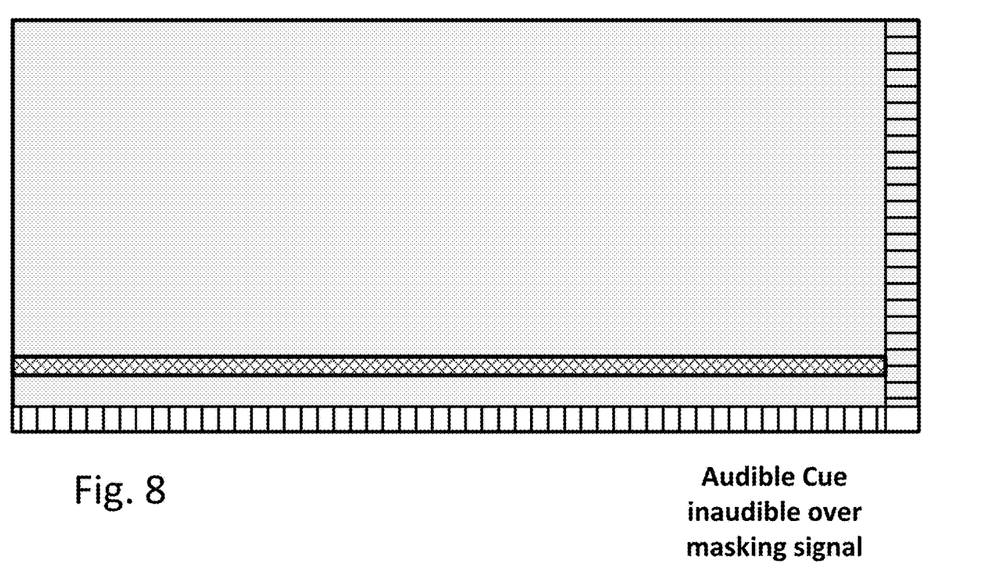
FIG. 8 is a sample spectrogram revealing that when presented together, the 400 Hz masking sound dominates the 440 Hz audible cue.

Referring briefly to FIG. 6, illustrated is a sample spectrogram showing a 440 Hz pure sine tone. This tone represents an audible cue (e.g., an alert) to be communicated to a user of a medical device. FIG. 7 is a spectrogram illustrating a 400 Hz masker signal. The masker signal will be the interfering ambient sound. FIG. 8 is a sample spectrogram revealing that when presented together, the 400 Hz masking sound dominates the 440 Hz audible cue. In this situation the 440 Hz audible cue will not be audible over the masker signal. The embodiments shown in FIGS. 2-5 seek to ameliorate this situation and enhance intelligibility of audible cues output by a medical device.

Figure 2:
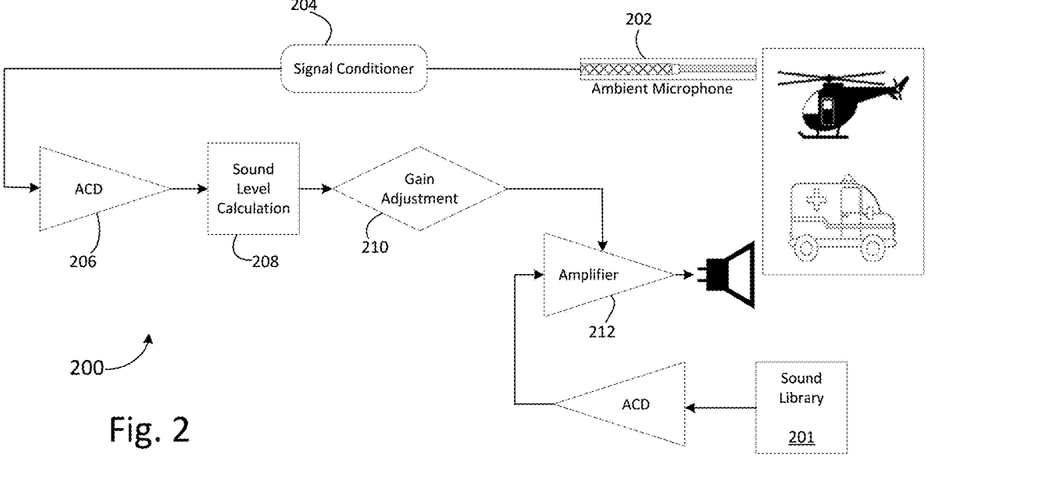
FIG. 2 is a functional block diagram generally illustrating core components of one basic embodiment.

FIG. 2 is a functional block diagram generally illustrating components of one basic embodiment. In this basic embodiment, a system 200 is implemented in a medical device and includes a microphone 202 to record the ambient noise being experienced in the environment and a library 201 of sound files which each represent audible cues. Each audible cue may be, in one implementation, a voice prompt or instruction for operating the medical device. In accordance with this embodiment, each sound file is processed to enhance intelligibility in loud environments. More specifically, the sound files may be processed to enhance harmonic signals of each audible cue, which serves to enhance the intelligibility of the audible cue, especially in louder environments. However, such processing may result in an audible cue which sounds somewhat harsh in quiet environments. Thus, it is desirable to output the audible cues at a volume that does not irritate the operator's hearing. Illustrative processing methods are illustrated in FIGS. 9-14 and described below.

The sound recorded using the microphone 202 is conditioned using signal conditioner 204 and converted from an analog signal to a digital signal using ADC 206. A sound level calculation component 208 then detects the sound level (e.g, volume) of the noise in the ambient environment. Using the detected sound level, a gain adjustment is applied to an amplifier 212 thus adjusting the sound level of audible cues such that it is appropriate for the current environment.

In various implementations, the gain adjustment 210 could be either an analog or digital control, with the latter depicted in FIG. 2. While offering intelligent adjustment of the sound level, this version offers basic improvement in resistance to auditory masking by ambient sounds.

Figure 3:
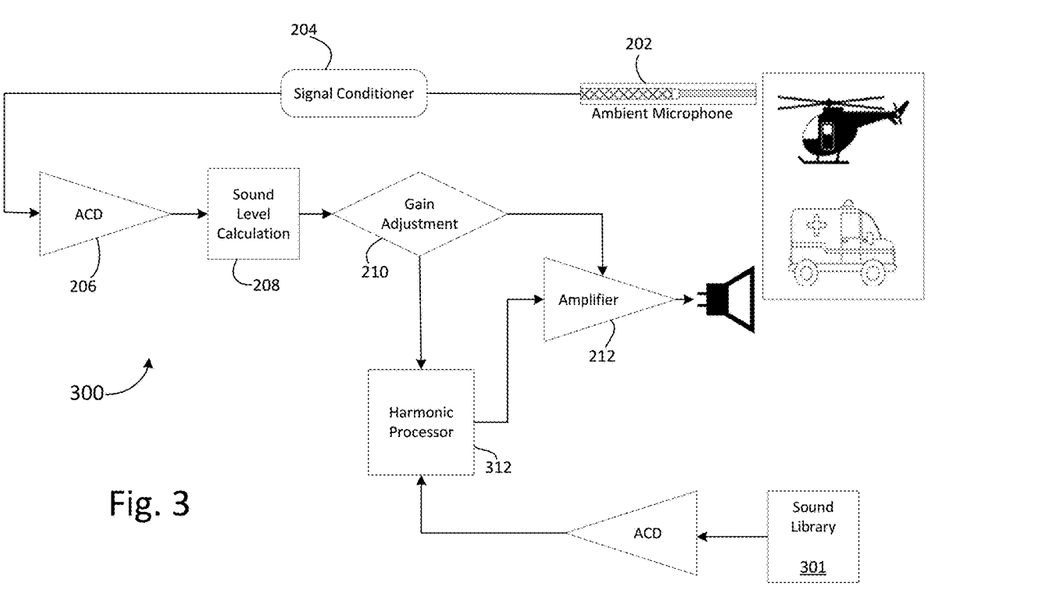
FIG. 3 is a functional block diagram illustrating components of a first alternative embodiment that improves on the basic embodiment of FIG. 1

FIG. 3 is a functional block diagram illustrating components of a first alternative embodiment 300 that improves on the basic embodiment of FIG. 1. Generally stated, components shown in FIG. 3 operate in the same manner as similarly-labeled components shown in FIG. 2. However, the sound files in the sound library 301 of the first alternative embodiment are somewhat less processed than those in the sound library 201 of the basic embodiment. Accordingly, the audible cues sound somewhat less harsh in quiet environments at the expense of some loss in intelligibility in more noisy environments.

The first alternative embodiment operates largely in a similar manner as the basic embodiment described above. Thus the sound level of the ambient noise of the environment is determined using a microphone 202 and sound level calculation component 208. However, the first alternative embodiment includes a harmonic processor 312 to add harmonically related frequency content to the audible cue to enhance intelligibility at higher sound levels. In other words, when the sound level calculation determines that the medical device is operating in a louder ambient sound level, the gain of the amplifier is increased to raise the sound level of the audible cue. In addition, the harmonic processor 312 dynamically alters the sound files to include harmonics that enhance the intelligibility of the audible cues in noisy environments. Accordingly, the audible cues sound less harsh in quiet environments where masking is less of a problem, but harshness is added (e.g., via third and fifth harmonics) to enhance intelligibility in a noisy environment.

As can be seen, the first alternative embodiment 300 produces more sound level when needed and also introduces harmonically-related spectral content to the output sound to enhance intelligibility at higher sound levels. The first alternative embodiment 300 improves greatly on the basic embodiment 200 for audibility in ambient noise.

Figure 4:
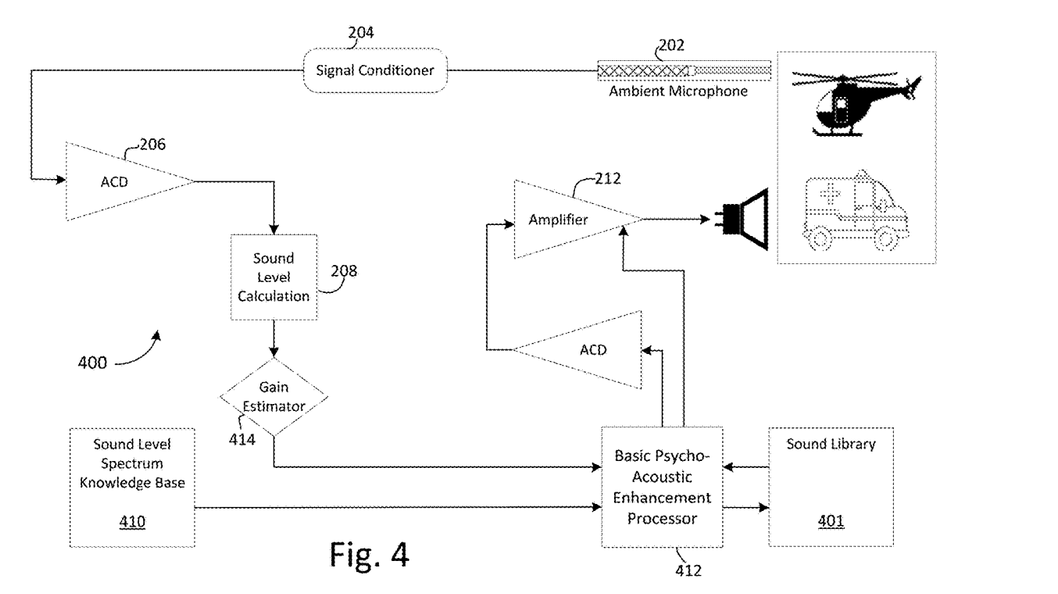
FIG. 4 is a functional block diagram illustrating components of a second alternative embodiment that improves on the first alternative embodiment of FIG. 3.

FIG. 4 is a functional block diagram illustrating components of a second alternative embodiment 400 that improves on the first alternative embodiment of FIG. 3. As above, components shown in FIG. 4 operate in the same manner as similarly-labeled components shown in FIGS. 2 and 3. However, the sound library 401 of the second alternative embodiment includes sound files that are more processed to enhance noisy-environment intelligibility (similar to the sound files used in the basic embodiment) and sound files that are less processed (similar to the sound files used in the first alternative embodiment). Accordingly, each of the audible cues may have at least two (but possibly more) corresponding sound files; at least one which sounds better in quieter environments and at least another that sounds better in louder environments. Of course, there may be certain audible cues for which alternative sound files are not necessary.

In accordance with this embodiment, a sound level spectrum knowledge base 410 is included which stores information about the spectral characteristics of typical maskers (i.e, competing noises which may mask the audible cues) in particular noise environments. In other words, based on prior evaluations and analysis, this embodiment incorporates a priori knowledge regarding particular noise contributors in various different ambient environments. In this manner, a basic psycho-acoustic enhancement processor (PAEP) 412 receives sound level information from the sound level calculation component 208 with an estimate of an appropriate gain that should be applied to a sound file based on the current ambient environment (via gain estimator 414).

The PAEP 412 uses the measurement of ambient sound level in combination with the knowledge base 410 of environmental noise levels. Based on (at least) those two inputs, the PAEP 412 determines which one of the several pre-processed sounds within sound library 401 best fit the ambient situation. Gain to the amplifier 212 may also be adjusted for enhanced use of the chosen pre-processed sound. The pre-processed sounds within library 401 have their spectral content adjusted based on one of many possible psycho-acoustic formulae for determining critical band frequencies of the basilar membrane. The spectral content of each specific sound is pre-processed to correspond with the various ambient sound level situations in the knowledge base 410.

FIG. 5 a functional block diagram illustrating components of a third alternative embodiment 500 that improves on the first and second alternative embodiments of FIGS. 3 and 4. As above, components shown in FIG. 5 operate in the same manner as similarly-labeled components shown in FIGS. 2, 3 and 4. However, the sound library 501 of the third alternative embodiment may include sound files that are less processed to enhance noisy-environment intelligibility (similar to the sound files used in the first alternative embodiment). The sound library 501 of the third alternative embodiment may, but need not, also include sound files that are more processed (similar to the sound files used in the basic embodiment) for noisy-environment intelligibility.

The third alternative embodiment 500 includes a microphone 202 and ancillary components to detect both sound level (i.e., sound level calculation component 208) and sound spectrum (i.e., sound spectrum analysis component 508) of the ambient environment. Measurements of those two parameters are used to create estimates of predicted auditory masking of the device sounds, via a spectrum enhancement estimation component 510. A psycho-acoustic model of changes to the source sound spectrum emerges in real-time which may be used to make the source sounds more resistant to masking in the presence of potentially masking sounds of the ambient environment. In this embodiment, an advanced PAEP 512 predicts necessary changes to both sound level and spectral content dynamically to enhance the sound output of the medical device for a given environment.

In most embodiments, a hold function (not shown) should be used to prevent changes to the sensed ambient sound level and adjustments to the sound output during the period when the device is itself generating sound (e.g., while playing an audible cue). This avoids making inappropriate adjustments based on the device contribution to the ambient environment.

Sample spectrograms will now be presented to help illustrate the operation of the above-described embodiments. In particular, the sample spectrograms shown in FIGS. 9-14 provide guidance regarding the processing of sound files for use in the embodiments illustrated in FIGS. 2-5 and described above. As with FIGS. 6-8, the "X" axis denotes time; 0 to 10 seconds. The "Y" axis represents frequency; 0 to 4000 Hz. Sound levels are represented by brightness on the spectrogram; brighter is higher sound level, darker is lower sound level.

Figure 9:
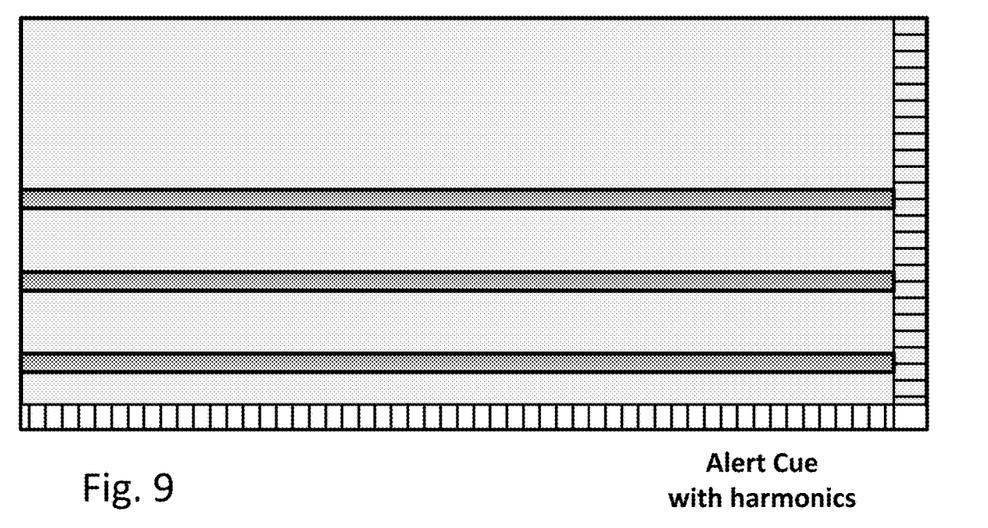
FIG. 9 is a sample spectrogram showing an audible cue processed to include harmonics of the audible cue.

FIG. 9 is a sample spectrogram showing an audible cue processed to include harmonics of the audible cue. Altering the sound spectrum of the audible cue such that energy is redistributed to the harmonics creates redundancies in non-overlapping auditory critical bands.

Figure 10:
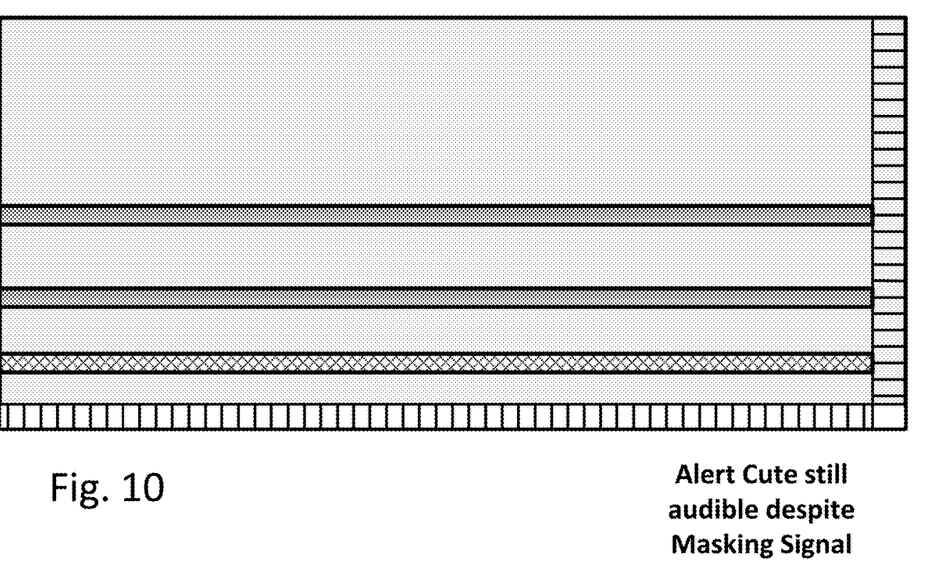
FIG. 10 is a sample spectrogram showing the altered audible cue of FIG. 9 in combination with the masker signal shown in FIG. 8.

FIG. 10 is a sample spectrogram showing the altered audible cue of FIG. 9 in combination with the masker signal shown in FIG. 8. As illustrated, when the 400 Hz single-frequency masker signal of FIG. 8 is presented with the altered audible cue of FIG. 9, the 400 Hz masker dominates the fundamental of the altered alert sound, but does not mask the higher harmonics. Thus, the altered alert audible cue is more robust to masking by a single frequency sound.

Figure 11:
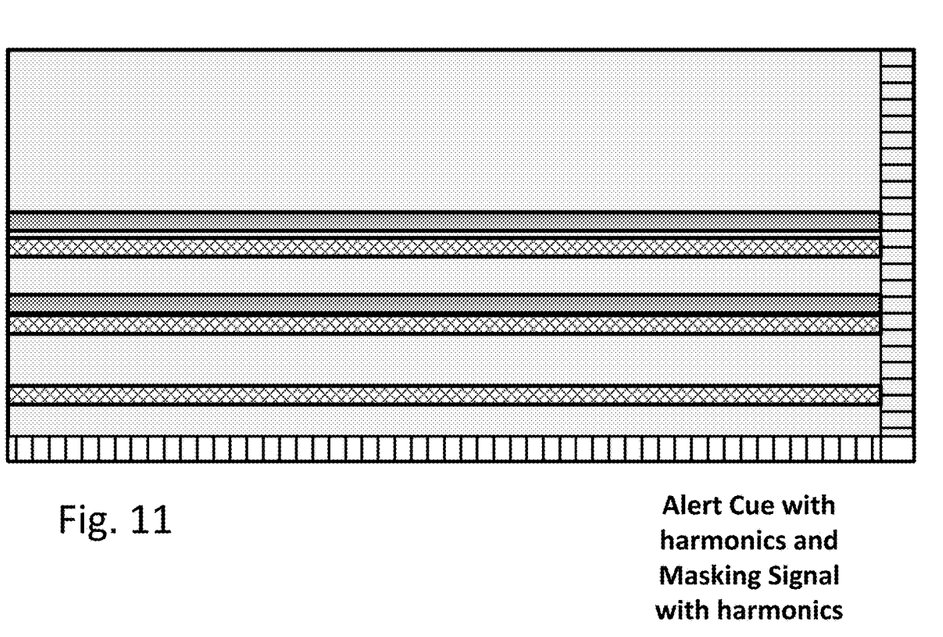
FIG. 11 is a sample spectrogram showing the altered audible cue of FIG. 9 in combination with a masker signal having harmonics.

FIG. 11 is a sample spectrogram showing the altered audible cue of FIG. 9 in combination with a masker signal having harmonics. As shown, if the altered audible cue may still be at risk of being hard to hear or even inaudible in the same environment as the masker signal with harmonic content. It will be appreciated that this depends on proximity of the masking sound harmonics to the altered audible cue harmonics and if they are both within a critical bandwidth of each other.

Figure 12:
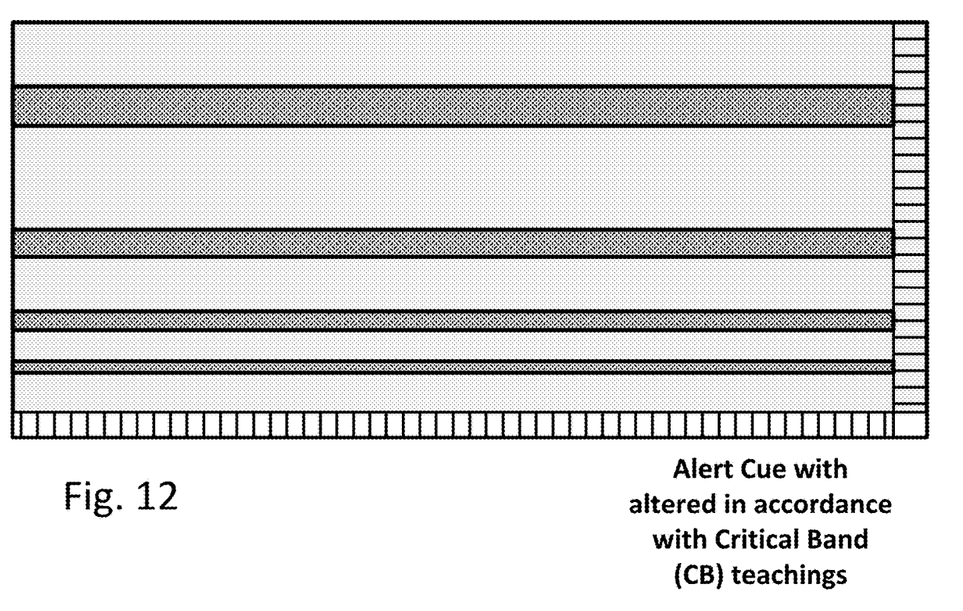
FIG. 12 is a sample spectrogram illustrating an audible cue altered in accordance with characteristics of the human auditory system.

FIG. 12 is a sample spectrogram illustrating an audible cue altered in accordance with characteristics of the human auditory system. More specifically, the adjustments to the audible cue are based on the psycho-acoustic concept of a Critical Bandwidth ("CB") that forms on the basilar membrane when stimulated. The basilar membrane is located within the cochlea in the inner ear. Generally stated, the critical bandwidth is the band of audio frequencies within which a second tone will interfere with the perception of a first tone by auditory masking. One such estimation of the critical bandwidth is presented below:

$$CB = 25 + 75[1 + 1.4(freq/1000)^2]^{0.69} \text{ Hz}^*$$

*Zwicker, Eberhard, Journal of Acoustical Society of America, November 1980
(This formula is but one example of many different equally-applicable formulae, as will be apparent to those skilled in the art.)

Figure 13:
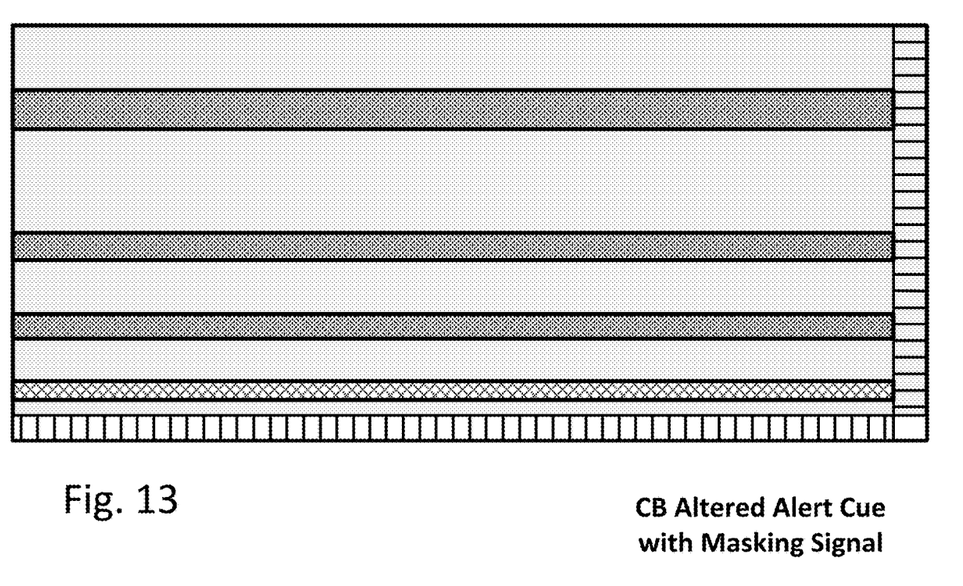
FIG. 13 is a sample spectrogram illustrating the critical band (described below) altered audible cue of FIG. 12 combined with the masking signal of FIG. 8.

FIG. 13 is a sample spectrogram illustrating the CB altered audible cue of FIG. 12 combined with the masking signal of FIG. 8. As is evident from FIG. 13, the CB altered audible cue is extremely robust to single frequency masking.

Figure 14:
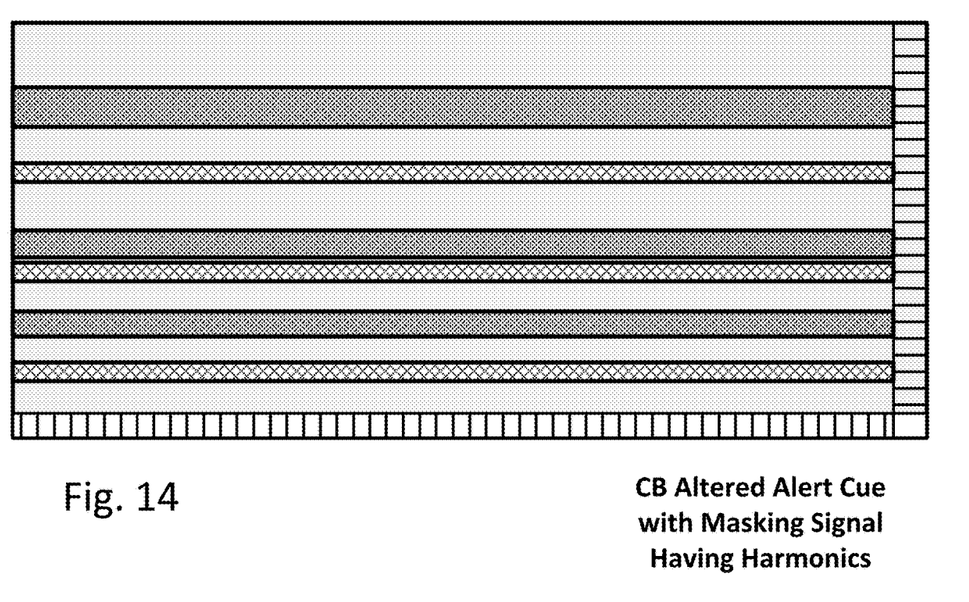
FIG. 14 is a sample spectrogram illustrating the critical band altered audible cue of FIG. 12 combined with the masking signal having harmonics.

FIG. 14 is a sample spectrogram illustrating the CB altered audible cue of FIG. 12 combined with the masking signal having harmonics. As is evident from FIG. 14, even when presented with a masking sound containing harmonic content, the CB altered audible cue remains audible as it is stimulating non-overlapping CBs of the basilar membrane and the spectral content is spread to avoid the harmonics of maskers.

In this description, numerous details have been set forth in order to provide a thorough understanding. In other instances, well-known features have not been described in detail in order to not obscure unnecessarily the description.

A person skilled in the art will be able to implement these additional embodiments in view of this description, which is to be taken as a whole. The specific embodiments disclosed and illustrated herein are not to be considered in a limiting sense. Indeed, it should be readily apparent to those skilled in the art that what is described herein may be modified in numerous ways. Such ways can include equivalents to what is described herein.

For example, in another embodiment for use in cars, trains, buses, planes, or other noisy environments in which audio announcements are made, a system may include a microphone configured to capture ambient noise; a sound library including a plurality of sound files, each sound file corresponding to an audible cue; an amplifier coupled to a speaker, the amplifier having a selectable gain and being configured to output each of the plurality of sound files over the speaker; a sound level detection component coupled to the microphone and configured to detect a sound level of the ambient noise; a sound spectrum detection component coupled to the microphone and configured to detect spectrum characteristics of the ambient noise; a sound spectrum analysis component coupled to the sound spectrum detection component and being configured to provide an estimate of an amount of gain to apply to tile amplifier based on an analysis of the spectral characteristics of the ambient noise; and a sound altering component configured to alter the selectable gain of tile amplifier based on the sound level of the ambient noise in conjunction with the estimate, or to alter harmonic content of the sound files based on the spectral characteristics of the ambient noise, or both.

In addition, various embodiments may be practiced in combination with other systems or embodiments. The following claims define certain combinations and subcombinations of elements, features, steps, and/or functions, which are regarded as novel and non-obvious. Additional claims for other combinations and subcombinations may be presented in this or a related document.

What is claimed is:

1. A system, comprising:
a microphone configured to capture first audio data representing a first sound in an environment;
a processor configured to:
determine a first frequency spectrum of the first sound;
retrieve, from a sound library, a sound file comprising second audio data representing a second sound;
compare the first frequency spectrum and a second frequency spectrum of the second sound; and
identify a harmonic frequency band of the second frequency spectrum that is non-overlapping with a portion of the first frequency spectrum; and
a speaker configured to output the second sound with the harmonic frequency of the second frequency spectrum.

2. The system of claim 1, wherein:
a sound level of the first sound is greater than or equal to a threshold sound level; and
the processor is further configured to modify the sound file to comprise a modified number of harmonics of the second frequency spectrum that is greater than or equal to a threshold number of harmonics, the sound file being modified to replace an initial number of harmonics in the second frequency spectrum with the modified number of harmonics, the initial number of harmonics being less than the threshold number of harmonics.

3. The system of claim 1, wherein the portion of the first frequency spectrum is a partial portion of the first frequency spectrum.

4. The system of claim 1, wherein the portion of the first frequency spectrum is an entire portion of the first frequency spectrum.

5. The system of claim 1, wherein:
the sound file is a first sound file that comprises a first number of harmonics of the second frequency spectrum;
the sound library further comprises a second sound file that comprises a second number of harmonics of the second frequency spectrum;
the second number of harmonics in the second file comprises the harmonic frequency utilized to output the second sound; and
the second number of harmonics is different from the first number of harmonics.

6. The system of claim 1, wherein:
the first audio data is captured during a time interval;
the sound file is a first sound file that comprises a first number of harmonics of the second frequency spectrum;
the sound library further comprises a second sound file that comprises a second number of harmonics of the second frequency spectrum;
the second number of harmonics in the second file comprises the harmonic frequency;
the second number of harmonics is different from the first number of harmonics; and
the speaker is configured to output, during the time interval, the second sound with the second frequency spectrum comprising the first number of harmonics, and to output, during a subsequent time interval, the second sound with the second frequency spectrum comprising the second number of harmonics.

7. The system of claim 1, wherein the sound file comprises a first number of harmonics of the second frequency spectrum, and the processor is further configured to modify the sound file to comprise a second number of harmonics of the second frequency spectrum, the second sound being an audible cue.

8. The system of claim 1, wherein:
the first audio data is captured during a first time interval;
the microphone is configured to capture, during a second time interval, third audio data representing a third sound in the environment that has a greater sound level than the first sound;
the processor is further configured to change the second frequency spectrum, which includes an initial frequency, to include the harmonic frequency; and
the speaker is further configured to output, during the first time interval, the second sound with the second frequency spectrum having the initial frequency, and to output, during the second time interval, the second sound with the second frequency spectrum having the harmonic frequency.

9. The system of claim 1, wherein:
the processor is configured to change an initial sound level of the second sound to a modified sound level that is greater than or equal to a threshold sound level: and
the speaker is configured to output, at the modified sound level, the second sound as a voice command or a voice instruction.

10. An electronic device, comprising:
a microphone configured to capture first audio data representing a first sound in an environment;
a processor configured to:
retrieve, from a sound library, a sound file comprising second audio data representing a second sound;
compare a first frequency spectrum of the audio data and a second frequency spectrum of the second audio data; and
identify a harmonic frequency band of the second frequency spectrum that is non-overlapping with a portion of the first frequency spectrum; and
a speaker configured to output the second sound with the harmonic frequency of the second frequency spectrum.

11. The electronic device of claim 10, wherein:
a sound level of the first sound is greater than or equal to a threshold sound level; and
the processor is further configured to modify the sound file to comprise a modified number of harmonics of the second frequency spectrum that is greater than or equal to a threshold number of harmonics, the sound file being modified to replace an initial number of harmonics of the second frequency spectrum with the modified number of harmonics, the initial number of harmonics being less than the threshold number of harmonics.

12. The electronic device of claim 10, wherein:
a sound level of the first sound is less than a threshold sound level: and
the processor is further configured to:
determine the sound file comprises an initial number of harmonics of the second frequency spectrum that is less than a threshold number of harmonics, and
refrain from modifying the sound file to replace the initial number of harmonics.

13. The electronic device of claim 10, wherein:
the microphone is configured to capture second audio data representing a third sound in the environment, the first sound being received by the microphone during an initial time interval that is prior to a subsequent time interval during which the third sound is received by the microphone, the first sound having a first sound level that is different from a second sound level of the third sound;
the processor is further configured to retrieve a second sound file comprising third audio data representing a fourth sound that is different from the second sound; and
the microphone is further configured to output the fourth sound during the second time interval.

14. The electronic device of claim 10, wherein:
the processor is further configured to:
determine a first sound level of the first sound as an ambient sound level; and
select a second sound level of the second sound that is greater than or equal to a sound level threshold; and
the speaker is further configured to output the second sound at the second sound level, the second sound being an audible cue.

15. The electronic device of claim 10, wherein:
the sound file is a first sound file, and the second sound is a first audible cue at a first sound level;
the processor is further configured to retrieve, from the sound library, a second sound file comprising third audio data representing a second audible cue; and
the speaker is further configured to:
output the first audible cue at a first sound level during a first time interval in which the first audio data is captured; and
output, during a second time interval, the second audible cue at a second sound level, the first sound being a first ambient sound at a first ambient sound level that is greater than a second ambient sound level of a second ambient sound received by the microphone during the second time interval.

16. A method of operating an electronic device, comprising:
identifying first audio data representing a first sound in an environment;
identifying a first frequency spectrum of the first sound;
retrieving, from a sound library, a sound file comprising second audio data representing a second sound;
comparing the first frequency spectrum and a second frequency spectrum of the second sound; and
identifying a harmonic frequency band of the second frequency spectrum that is non-overlapping with a portion of the first frequency spectrum; and
outputting the second sound with the harmonic frequency of the second frequency spectrum.

17. The method of claim 16, wherein the second sound is an audible cue, further comprising:
selecting the audible cue from the sound library.

18. The method of claim 16, wherein a sound level of the first sound is greater than or equal to a threshold sound level, further comprising:
modifying the sound file to comprise a modified number of harmonics in the second frequency spectrum that is greater than or equal to a threshold number of harmonics, the sound file being modified to replace an initial number of harmonics in the second frequency spectrum with the modified number of harmonics, the initial number of harmonics being less than the threshold number of harmonics.

19. The method of claim 16, where a sound level of the first sound is less than a threshold sound level, further comprising:
determining the sound file comprises an initial number of harmonics in the second frequency spectrum that is less than a threshold number of harmonics; and
refraining from replacing the initial number of harmonics of the second frequency spectrum in the sound file.

20. The method of claim 16, wherein:
a sound level of the first sound is less than a threshold sound level;
the sound file is a first sound file; and
retrieving the first sound file further comprises retrieving the first sound file from among the first sound file and a second sound file, a first number of harmonics of the second frequency spectrum being less than a second number of harmonics of a third frequency spectrum of a third sound, the third sound being represented by third audio data in the second sound file.

* * * * *